United States Patent [19]

Ruge

[11] Patent Number: 4,917,109

[45] Date of Patent: Apr. 17, 1990

[54] PATIENT RESTRAINT GARMENT

[75] Inventor: Randal R. Ruge, Swanton, Ohio

[73] Assignee: R. R. Ruge, Inc., Toledo, Ohio

[21] Appl. No.: 307,461

[22] Filed: Feb. 8, 1989

[51] Int. Cl.[4] .............................................. A61F 5/37
[52] U.S. Cl. ................................. 128/874; 2/DIG. 7
[58] Field of Search ............... 128/846, 869, 870, 871, 128/873, 874, 875, 876; 2/326, 327, 328, DIG. 7

[56] References Cited

U.S. PATENT DOCUMENTS

| | | | |
|---|---|---|---|
| 1,651,561 | 12/1927 | Storey | 119/96 |
| 2,062,586 | 12/1936 | Lawrence | 128/875 |
| 2,077,244 | 4/1957 | Le Roy | 297/465 |
| 2,782,783 | 2/1957 | Gay | 128/874 |
| 3,136,311 | 6/1964 | Lewis | 30/345 |
| 3,181,530 | 5/1965 | Storey | 128/874 |
| 3,265,065 | 8/1966 | Jillson | 128/874 |
| 3,276,432 | 10/1966 | Murcott | 119/96 |
| 3,323,150 | 6/1967 | Rehder | 128/872 |
| 3,742,945 | 7/1973 | Reinhardt | 128/874 |
| 3,788,309 | 1/1974 | Zeilman | 128/874 |
| 3,889,668 | 6/1975 | Ochs et al. | 128/875 X |
| 4,117,840 | 10/1978 | Rasure | 128/874 |
| 4,205,670 | 6/1980 | Owens | 128/875 |
| 4,330,152 | 5/1982 | Legan | 297/465 |
| 4,396,013 | 8/1983 | Hasslinger | 128/845 |
| 4,571,000 | 2/1986 | Holder | 297/465 |
| 4,744,354 | 5/1988 | Triunfol | 128/875 |

Primary Examiner—Richard J. Johnson
Assistant Examiner—Lynda M. Cofsky
Attorney, Agent, or Firm—Robert E. Witt

[57] ABSTRACT

A patient restraint garment, which is quickly applied to or removed from a patient and which is substantially non-defeatable by the patient, is disclosed which comprises: a flexible panel having an opening to receive the head and neck of a patient thereby forming front and rear portions covering the upper torso of the patient; tying straps attached to the bottom corners of the front portion of the panel for engagement with at least one of a plurality of loops attached to the bottom region of the rear portion of the panel, to connect and snug the bottom regions of the front and rear portions of the panel about the patient, prior to securing the tying straps to a structure out of reach of the patient, at least one side strap extending laterally from each side of the front portion of the panel, at chest level, which straps have fastening means thereon for engagement with a portion of a receiving means attached to the upper back region of the rear portion of the panel to create custom-fit, adjustable arm holes for each patient and to connect and snug the chest region and the upper back region of the front and rear portions respectively of the panel about the patient; and a downwardly extending flap attached to the rear portion of the panel above the receiving means, which flap has fastening means for subsequent engagement with another portion of the receiving means, thereby covering the engaged side straps, preferably in a snugging relationship with the engaged side straps, to provide a locking means for the engaged side straps out of reach of the patient.

12 Claims, 2 Drawing Sheets

PATIENT RESTRAINT GARMENT

BACKGROUND OF THE INVENTION

This invention relates to restraint garments for restraining passive patients and particularly to garments for restraining incorrigible patients of all ages and sizes, especially those patients under the influence of drugs and/or alcohol and/or mental dysfunction, to provide protection to the patient as well as to attendants.

More specifically, this invention relates to a restraint garment for restraining movement of the upper torso of a patient while allowing freedom of limb movement, which enables an attendant to quickly custom-fit the garment about the patient, and which prevents the patient from defeating the imposed restraint under most circumstances.

Restraint garments have found particular utility in controlling the actions and in limiting the mobility of a patient/user for various reasons, including passive people who may be infirm, senile, or recovering from surgery, and aggressive people who may be under the influence of drugs, alcohol or mental dysfunction. Additionally, some restraint garments have been used for children, for many occasions, and for injured people, especially those who have lost their motor functions.

Pediatric restraints have been used to secure infants to a bed or chair, to inhibit movement sideways or lengthwise, and combination bibs/restraints have been used for safely holding and securing a child in a structure to prevent a fall or other injury.

Adult restraints have been used to restrict excessive movement of a person laterally and/or longitudinally, with various degrees of limb movement available to the person. The confinement of a person is generally to a bed, chair, wheelchair or other similar structure, for the various reasons stated.

For the most part, attention has been given to such garments regarding the comfort of the person so that abrasions and sores do not result, and regarding the safety of the person so that they are not injured such as by impaired circulation or by strangulation, and regarding the anxiety and panic syndrome on the part of the wearer, which can lead to flailing limbs and/or to depression.

Some restraints have taken the form of jackets, vests with wing straps which wrap around the patient, and pull-overs which cover at least the upper torso of the person, each having variations of belts, straps, loops, hooks, eyelets, lacing, buttons, clasps, clamps, buckles and other fasteners including the hook-loop interacting materials known as Velcro.

Restraint garments have been produced from flexible materials, usually a fabric, and a few have head openings to slip over the person's head, some of which openings comprise a lacing and a protective tongue between the lacing and the person. Dual strap abdominal support sections on the lower anterior portion of a garment have been employed, as well as multipaneled garments connected by ties.

Various limitations exist with the previous restraint garments, but one of the greatest drawbacks includes the ability of the patient to defeat the restraint, through large arm openings and/or via fasteners or tying straps within reach of the patient, whereby the patient negotiates a way free, leading to serious consequences to the patient and/or to the attendants physically, and to the facility housing the patient regarding liability claim potential.

Further limitations of some restraint garments include the development by the patient of abrasions from bulky construction or from various fasteners, which abrasions can become infected. Additionally, some restraints are too restrictive regarding the movement of the upper torso of the patient, leading to bed sores.

Other restraint garments have employed various strapping devices which have led to psychological chaos of patients when they are restrained. And, some restraint garments are cumbersome for attendants and are time consuming to apply and/or to remove from patients, due in part to the presence of fixed or permanent arm openings.

Until the present time, the primary means for attendants to restrain aggressive patients was to employ restraint garments which unduly restrained the patients.

SUMMARY OF THE INVENTION

The present invention however, provides a restraint garment with means to prevent the person being restrained from defeating the restraint, while providing non-abrasive comfort and substantial upper torso restriction and limb movement to the person being restrained, and means to facilitate quick, easy application, fitting and removal of the restraint garment, thus overcoming the above limitations by employing in combination with other elements, receiving means strategically located on the garment to sequentially hold a plurality of straps each having fastening means and at least one flap having fastening means.

The restraint garment of the present invention is preferably fabricated from a flexible panel of fabric or cloth which is durable, washable, and is capable of folding and of contouring about the upper torso of the wearer, in combination with (1) long tying straps extending laterally from the bottom corners of the anterior portion of the panel, (2) receiving means located on the bottom area of the posterior portion of the panel to receive the tying straps in various modes, (3) at least one pair of straps attached to the sides of the panel and extending laterally from the upper chest region of the anterior portion of the panel, each having fastening means attached to their free ends, (4) at least one flap attached to the upper back region of the posterior position of the panel, each having fastening means attached thereto, and (5) at least one receiving means attached to the upper back region of the posterior portion of the panel below the attachment of the flap, to sequentially receive the side straps and the flap.

The tying straps provide multiple functions during the operational mode of the garment, and are typically flexible and durable. The tying straps are preferably of a suitable length for tying to a structure out of reach of the patient, after engaging the receiving means on the lower posterior portion of the panel which provides communication between the lower areas of the anterior portion and the posterior portion of the panel, and allows for snugging of the same about the patient.

The receiving means for engaging the tying straps are preferably a plurality of flexible, durable loops of the same material as the tying straps, comprising at least two pair of loops attached to the bottom region of the posterior portion of the panel. One such pair of loops is disposed proximal to and on either side of the central longitudinal axis of the panel, and the other pair of loops is disposed proximal to the sides of the bottom region of the posterior portion of the panel in transverse or horizontal alignment, generally to accommodate various operational modes of engaging the tying straps, depending upon whether the patient will be supine or sitting and/or whether the patient is passive or aggressive. Additional loops or pairs of loops can be disposed between the above loops when desired for variation of the operational modes of engaging the tying straps.

The side straps are generally shorter in length than the tying straps and are preferably of the same material as the tying straps. The side straps provide multiple functions during the operational mode of the garment, including furnishing communication between the anterior portion and the posterior portion of the panel at the axillae regions of the patient. More specifically, the side straps provide adjustable arm openings, in situ, on the patient, which can be adjusted to control the snugness of the garment at the axillae region of the patient. Furthermore, the side straps have attached thereto, preferably along the length of one surface thereof, fastening means for engagement with receiving means attached to the upper back region of the posterior portion of the panel, for quick, easy fitting and/or removal of the garment about the patient and as part of an anti-tamper system for the garment.

The flap is preferably fabricated of the same fabric as the panel, but generally can be constructed from material which is flexible and durable and washable and which is capable of contouring to the upper back region of the wearer. The flap, attached to the upper back region of the person wearing the garment, provides multiple functions during the operational mode of the garment, including covering the attached side straps, and locking the side straps, in situ, in position on the receiving means, via fastening means attached to the lower area of the free end of the flap, and preferably transversely attached thereto.

The fastening means, attached to the side straps and to the flap, and the receiving means, attached to the upperback region of the posterior portion of the panel, are preferably constructed of Velcro or Velcro-like materials comprising a two component system of interlocking flexible materials. The fastening means is preferably the component material comprising a plurality of loops, and the receiving means is preferably the component material comprising a plurality of hooks, which loops and hooks readily interact to hold the two components together.

The side straps, during the operational mode of the restraint garment, when being worn by a patient, preferably extend in a generally upward direction from their points of attachment on the anterior portion of the panel to their areas of attachment on the receiving means located on the upper back region of the posterior portion of the panel. This upwardly extending direction of the side straps assists in closing or decreasing the areas of the arm openings in addition to that provided by the degree of tightness or looseness of the side straps, to provide adjustable arm openings to meet various conditions presented by the size and/or behavior of the patient.

The receiving means located on the posterior portion of the panel, and generally on the upper back area of the patient during the operational mode thereof, is preferably constructed of a single common area, to receive the side straps and the flap. The receiving means is preferably of sufficient width to transverse the width of the panel, and is preferably of sufficient height to receive all or portions of the fastening means attached to the side straps and all or a substantial portion of the fastening means attached to the flap.

The receiving means may also be constructed of a plurality of Velcro or Velcro-like materials (not shown) to further accommodate the interrelationship between the fastened side straps and the covering flap attached thereto.

The fastening means attached to the side straps is preferably of a length to substantially cover the length of the side strap, and is preferably of a width to substantially cover the width of the side strap.

The fastening means attached to the flap is preferably a strip, or may comprise multiple strips, transversing the width of the panel proximal to the free end of the flap.

The fastening means of the side straps, and hence the side straps themselves, may be aligned on the receiving means in an end-to-end relationship, or a parallel relationship, or a stacking relationship, or an overlapping relationship, and the fastening means of the flap may be in a touching or a non-touching relationship to the fastened side straps on the receiving means, when the flap is made to cover the fastened side straps. The flap preferably covers the attached side straps in a snugged relationship, but a loose fitting relationship of the flap to the attached side straps is tolerated during the operational mode of the garment.

The receiving means and the fastening means readily interact by the application of slight pressure of one to the other to form a strong bond, which upon the application of a "ripping" or "tearing" or "pulling" action under controlled conditions of, for example, the fastening means from the receiving means, the bond is released, whereby both means are reusable for bonding at another time. However, when a tensile force is applied to the bond, such as, for example, by a patient trying to defeat the engagement of the fastening means to the receiving means, disengagement of the bond requires a tensile force beyond the capabilities of most patients, especially as the surface area of the bond increases. A compressive force does not appear to disengage the bond since both means are flexible and compress with the force.

With the above discussion, it can be appreciated that when the side straps are attached to the receiving means during the operational mode of the restraint garment about the person/patient, and the flap is subsequently attached to the receiving means to cover the attached side straps, out of reach of the person/patient, a flexible locking means is produced which is substantially non-defeatable by the person/patient.

One advantage then of the present invention is that the restraint garment is easily and quickly positioned on and fitted to the person/patient without undue fear to the person/patient, and the garment is easily and quickly removed from the person/patient by an attendant. Another advantage of the present invention is that the upper torso of the person/patient is restricted while allowing limb movement, and the arm openings are adjustable to fit each person/patient to provide a substantially non-defeatable garment by preventing escape of the arm therethrough by the person/patient. Another advantage of the present invention is that the garment is adjustable to various body sizes, male and female, without requiring protective material between the adjusting means and the person/patient. Yet another advantage of the present invention is that a flexible locking means, featuring quick fasten/release means, is provided on the upper back area of the posterior portion of the panel during the operative mode of the garment which is non-abrasive and does not interfere with the comfort of the person/patient. Still another advantage of the present invention is that the garment is adjustable for a restricted supine position or a 90° rotatable supine position, and is adjustable for a restricted sitting position or a 90° rotatable sitting position. Still another advantage of the present invention is that the restraint garment is of simple construction which renders it inexpensive to manufacture and to clean, and which renders it capable of being fitted/worn over or under other clothing of the person/patient.

The present invention has proven to be well suited to restrain a person/patient without undue discomfort or fear, by restricting the upper torso of the person/patient while allowing limb movement of the person/patient, via the use of a flexible panel in combination with adjustable arm openings, adjustable tying straps, and a flexible locking means out of reach of the person/patient, to provide a substantially nondefeatable restraint.

It is therefore an object of the present invention to provide a garment for a person/patient to be restrained without undue discomfort or fear, while minimizing potential danger of self-harm and escape from the garment.

It is another object of the present invention to provide a restraint garment which is quickly and easily fitted to and removed from a person/patient by an attendant, under controlled conditions and under volatile conditions.

It is yet another object of the present invention to provide a restraint garment which restricts the upper torso of a person/patient, while allowing limb movement.

It is yet another object of the present invention to provide a restraint garment comprising communicating means between anterior and posterior portions of a panel, to allow adjustment of the garment to various body sizes.

It is still another object of the present invention to provide a restraint garment which is of simple construction and is inexpensive to manufacture and to clean and which can be worn over/under other clothing of the person/patient.

It is still another object of the present invention to provide adjustable arm openings and adjustable restraint modes of the person/patient while sitting or while supine.

It is a further object of the present invention to provide a flexible locking means on the restraint garment, out of reach of the person/patient.

This invention makes possible the use of commercially available hook and loop material, more commonly referred to as Velcro (registered trademark), in combination with straps, a panel of fabric, and a covering flap, to produce a flexible locking means which functions in an improved manner different than available closures, by attaching the loop material (fastening means) to the straps and to the flap, and by attaching the hook material (receiving means) to a specific region of the panel, and by engaging the straps and the flap sequentially to the specific region of the panel.

More specifically, the operation of the flexible locking means on the restraint garment of this invention or on other garments, involves the engagement of the straps having fastening means attached thereto to one area of the receiving means on the panel, followed by the engagement of the flap having fastening means attached thereto to another area of the receiving means on the panel, the latter of which covers the attached straps, and the resulting "locking" of the attached straps by the attached flap is not substantially disturbed by compressive forces or by tensile forces acting substantially parallel to the longitudinal axis of the attached straps and/or to the plane of the panel. A tangential and/or twisting and/or angular force is required to "unlock" the engaged components of the flexible locking means.

According to the present invention, the restraint garment is fitted to a person/patient easily and quickly by an attendant, while maintaining the dignity and comfort of the person/patient, and which garment is not abrasive or harmful to or defeatable by the person/patient but provides various operational modes for the person/patient, thereby improving the safety considerations to the person/patient and limiting the liability considerations to the attendant and/or to the medical institutions, since a tangential and/or twisting and/or angular force is required to "unlock" the engaged components of the flexible locking means and such force(s) is generally not available to the person/patient due to the location of the flexible locking means on the garment.

One essential feature of the restraint garment of the present invention is the use of a flexible locking means as herein disclosed in a region out of reach of the person/patient, to fix and to secure the side straps after adjustment of the arm openings and adjustment of the upper portion of the garment to the person/patient.

Another essential feature of the restraint garment of the present invention, in combination with the above feature, is the use of tying straps and their receiving means as herein disclosed to provide various operating mode positions available to the person/patient and to allow adjustment of the lower portion of the garment to the person/patient, prior to tying such straps to a structure out of reach of the person/patient.

A critical feature then, when employing the flexible locking means of this invention in combination with the panel and straps of the restraint garment of the present invention, is its location on the panel, which is at the approximate level of an imaginery line extending from axilla to axilla of the person/patient when the garment is in the operational mode, which location is generally out of reach of most persons/patients and/or prevents the person/patient from gaining needed leverage to apply a twisting, angular force, such as by "ripping" or by "tearing" the attached straps from their receiving means.

DETAILED DESCRIPTION OF THE PREFERRED EMBODIMENT

Figure 1:
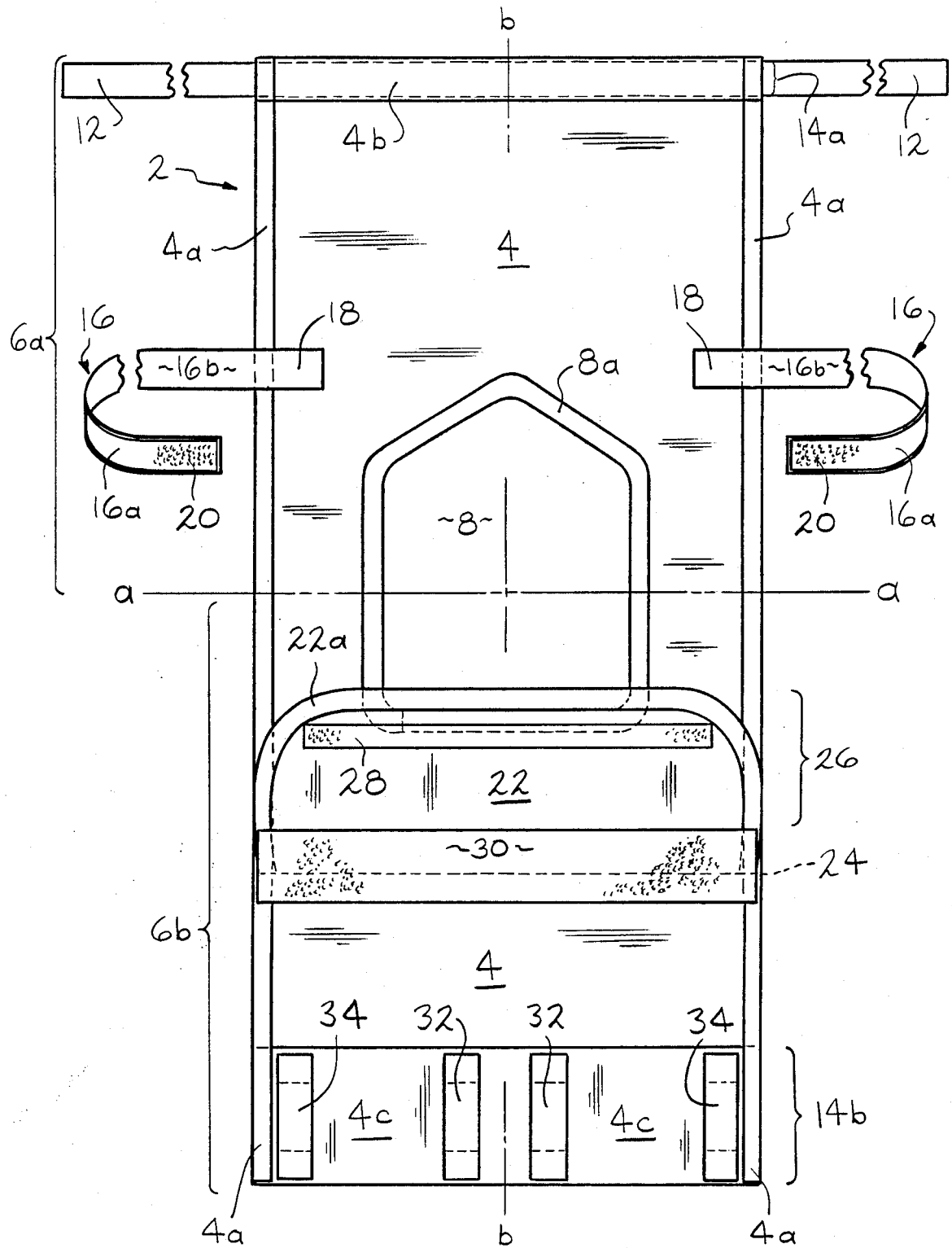
FIG. 1 is a plan view of the invention.

The restraint garment of this invention finds particular utility in the medical professions and related industry, where restraint of a person may be deemed necessary to protect the person/patient and/or to protect the attending personnel.

Specifically, the restraint garment of this invention is useful in situations where the person/patient is infirm or has a specific disability or is recovering from various medical procedures or exhibits aggressive, threatening, violent behavior, whereby the person/patient must be restrained with a minimum of fear and discomfort in a quick and easy manner by one or more attendants, and the restraint must not harm the person/patient during its operational mode whether by normal movements of the person/patient or by contortions or violent movements exhibited by a person/patient when trying to gain freedom.

In the construction of the restraint garment of this invention, it is important that washable, flexible, foldable materials which are non-irritating and of durable integrity be employed for all the components thereof. Preferably, the panel and the flap are of the same material, e.g. polyester/cotton blend, and the straps and strap-holding loops comprise a durable material which is flexible and foldable and non-irritating, e.g. nylon strapping, and the fastening means/receiving means are releasably interactive and comprise a durable, flexible, foldable material which is non-irritating, e.g. Velcro or Velcro-like materials. It is also important that the restraint garment have adjustments for various body sizes and that it have adjustments for arm openings, which adjustments are secured out of reach of the person/patient and that it provide various modes of restriction of the person/patient.

These requirements indicate the necessity for providing a flexible locking means on the posterior portion of the panel, out of reach, at the approximate upper back region of the person/patient when the restraint garment is in the operative mode, to maintain the adjustments regarding the fitting and the arm openings without discomfort to the person/patient. Furthermore, these requirements indicate the necessity for providing receiving means on the posterior portion of the panel at its lower area, to receive the tying straps from the anterior portion of the panel, and to vary the degree of restriction of the person/patient during the operational mode of the restraint garment from no rotational movement to 90° rotational movement.

Therefore, it becomes crucial that the receiving means of the flexible locking means provide a suitable area to receive the fastening means of the arm opening/body fitting straps and the fastening means of the overlapping flap, wherein this suitable area may comprise a single area as shown in the drawings or may comprise a plurality of areas (not shown). And, it becomes crucial that the receiving means for the longer tying straps comprise at least two pair of strap-holding loops as shown in the drawings or comprise at least four pair of slits (not shown).

At least one foldable flap with fastening elements for secured relation with the panel to provide a protective covering channel to accommodate fastening straps previously in secured relation with the panel, is herein referred to as the flexible locking means.

Figure 2:
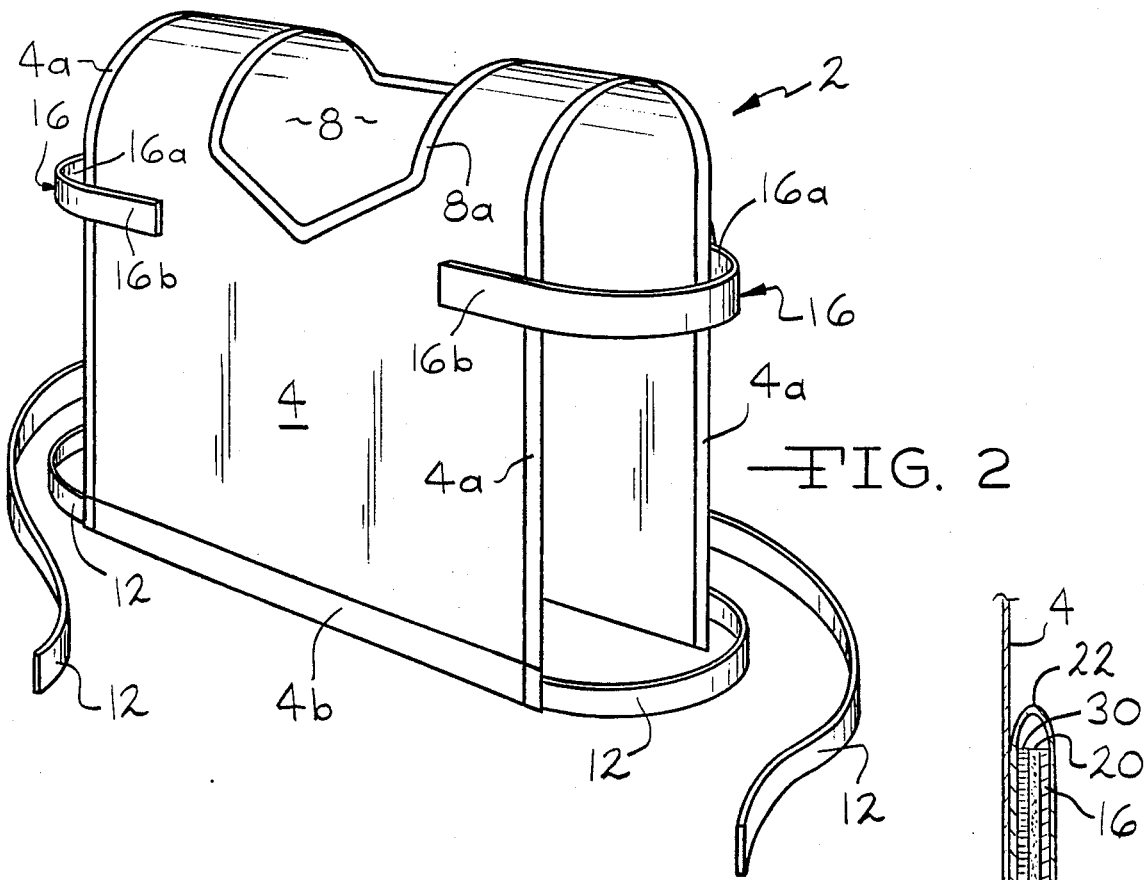
FIG. 2 is a front perspective view of the invention.
Figure 3:
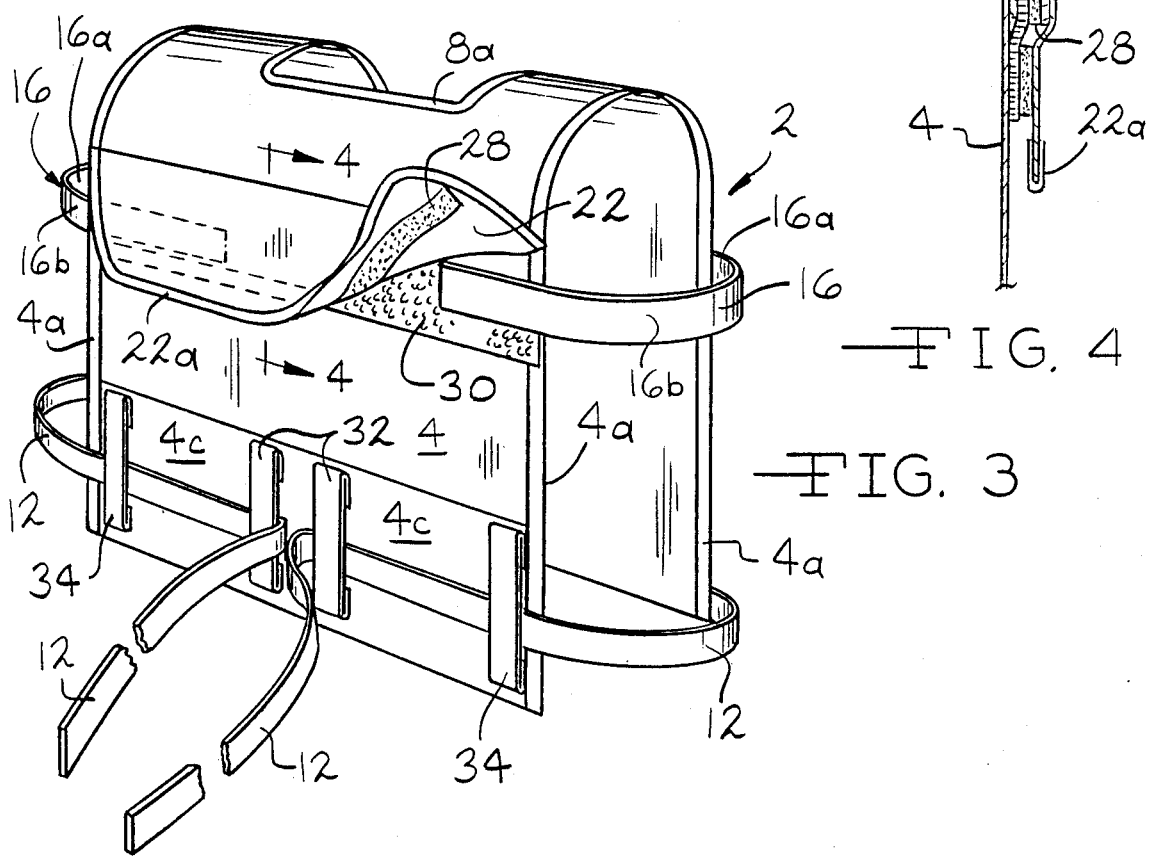
FIG. 3 is a rear perspective view of the invention, showing a flap in a partially closed position.

Referring to FIG. 1, the restraint garment 2 is shown in the non-operational mode as a rectangular panel 4 of a foldable flexible material. An opening 8 juxtaposed about the intersection of the central transverse axis a-a, and central longitudinal axis b-b in panel 4 is provided to receive the head/neck of a person/patient so that panel 4 drapes about the upper torso of the person/patient during the operational mode of the garment 2 as shown in FIG. 2 and FIG. 3. Line a-a, defining the central transverse axis of panel 4, is the approximate dividing line between the anterior portion 6a and the posterior portion 6b of panel 4, formed by draping panel 4 over the upper torso of the person/patient during the operational mode of the garment 2, depending upon the body size of the person/patient.

The material of panel 4 may comprise conventional fabric which is durable, non-abrasive and washable, and may comprise a close weave or an open weave. A binding 4a or piping is preferably provided by conventional attachment, such as by bonding and/or by stitching, along the longitudinal edges of panel 4 for strength, aesthetics and comfort to the person/patient during the operational mode of the garment 2. Lower area 4b of the anterior portion 6a of panel 4 is preferably provided by folding panel 4 upon itself at a height 14a which preferably approximates or is slightly greater than the width of strap material employed to form at least one pair of tying straps 12, 12. The folding of lower of panel 4 upon itself produces a channel or pocket 4b which is retained by the above-described conventional means independently of or concurrently with the attachment of the strap material to panel 4.

The strap material referred to above is preferably a single continuous length and is preferably attached within the channel or pocket of the lower area 4b of panel 4 by the above-described conventional means, to provide laterally extending tying straps 12, 12. The tying straps 12, 12 are of sufficient length to enable engagement with receiving means located on lower area 4c of the posterior portion 6b of panel 4 represented as two pair of strap-holding loops 32, 32 and 34, 34, prior to being tied to a structure out of reach of the person/patient.

Lower area 4c of the posterior portion 6b of panel 4 is preferably provided by folding panel 4 upon itself at a height 14b which preferably approximates or is slightly greater than the length of the strap-holding loops 32, 32 and 34, 34. The folding of lower area 4c onto panel 4 produces a pocket or a double layer of fabric which is retained by the above-described conventional means for strength, aesthetics and comfort to the person/patient during the operational mode of the garment 2.

The one pair of strap-holding loops 32, 32 is attached to the double layer of fabric provided by lower area 4c of the posterior portion 6b of panel 4 and is preferably slightly spaced and disposed proximal to and on opposite sides of the central longitudinal axis defined by line b-b of panel 4. The other pair of strap-holding loops 34, 34 is attached to lower area 4c of the posterior portion 6b of panel 4 and is preferably substantially spaced and disposed distal to and on opposite sides of the central longitudinal axis b-b of panel 4, approaching or contacting the binding 4a or piping of panel 4. The attachment of the two pair of strap-holding loops 32, 32 and 34, 34 is preferably to the double layer of fabric provided by lower area 4c of panel 4, and is accomplished by the above-described conventional means. However, when slits are employed (not shown) as the receiving means for tying straps 12, 12, the pocket formed at lower area 4c of panel 4 may be utilized.

The material for the strap-holding loops 32, 32 and 34, 34 is preferably of the same material as the strap material employed for the tying straps 12, 12. The loop size of the strap-holding loops 32, 32 and 34, 34 should be suitable to freely accommodate tying straps 12, 12, and is preferably double the approximate width of the strap material of tying straps 12, 12 to accommodate a stacking or a side by side arrangement thereof during the operational mode of the garment 2.

The restraint garment 2 further comprises at least one pair of opposed, laterally extending flexible fastening straps 16, 16 attached at ends 18, 18 by the above-described conventional means to either side at the approximate mid-height of anterior portion 6a of panel 4, or at the approximate chest level of the axillae regions of a person/patient when the garment 2 is in the operational mode. Flexible fastening means 20, 20, preferably of Velcro or Velcro-like material comprising a plurality of loops, is attached to surfaces 16a, 16a of each of the flexible fastening straps 16, 16, preferably the interior surfaces thereof, by the above-described conventional means, thereby leaving the other surfaces 16b, 16b of each of the flexible fastening straps 16, 16, preferably the outside surfaces thereof, with their normal smooth non-irritating characteristics. The lengths of the flexible fastening straps 16, 16 are sufficient to extend under the arms of persons/patients of varying body size for engagement with receiving means 30 attached to the approximate mid-height of the posterior portion 6b of panel 4, or at the approximate axillae level of a person/patient during the operational mode of the garment 2.

A substantially rectangular foldable flexible material 22 is attached to the posterior portion 6b of panel 4 by the above-described conventional means to provide a flap structure. Flap 22 is shown in the open position as represented by 26, and further comprises binding 22a or piping attached thereto by the above-described conventional means. Flexible fastening means 28, preferably of Velcro or Velcro-like material comprising a plurality of loops, is attached by the above-described conventional means to flap 22 on the interior surface thereof for engagement with receiving means 30 during the operational mode of the garment 2.

The flap 22 preferably has rounded corners but may have square corners to further prevent tampering by a person/patient during the operational mode of the garment 2. Fastening means 28 is preferably located proximal to the transverse free edge of flap 22, to provide sufficient unencumbered area on flap 22 to cover straps 16, 16 during the operational mode of the garment 2. Flap 22 may also have spaced apart fastening means (not shown) which are capable of straddling the engaged fastening straps 16, 16.

Flexible locking means, represented by receiving means 30, straps 16, 16 with fastening means 20, 20, and flap 22 with fastening means 28, acting in concert with panel 4, provides the basis for maintaining adjustments of the garment 2 to the person/patient during the operational mode thereof, hereinafter described in greater detail.

Receiving means 30 may be attached to posterior portion 6b of panel 4 contiguous with the area of attachment of flap 22 or proximal to the area of attachment of flap 22 or covering the area of attachment of flap 22 to panel 4. Receiving means 30 must be of sufficient area to receive straps 16, 16 on one portion and the fastening means 28 of flap 22 on another portion, so that flap 22 covers and locks in place the attached straps 16, 16 during the operational mode of garment 2. Further, the area of receiving means 30 may be a single area (shown) or may be multiple areas (not shown) to accommodate the above requirements.

Receiving means 30 is preferably fabricated of Velcro or Velcro-like material comprising a plurality of hooks for engagement of the interactive loops of fastening means 20, 20 on straps 16, 16 and of fastening means 28 on flap 30.

Referring to FIG. 2 and to FIG. 3, the restraint garment 2 is shown in the operative mode, but without the showing of the upper torso of the person/patient. As panel 4 is placed over the head/neck of the person/patient via opening 8, which may be of configurations other than as shown, panel 4 naturally drapes about the front and the back of the upper torso of the person/patient. Bindings 4a, 8a and 22a are attached respectively to the longitudinal edges of panel 4, the edges of opening 8 and the edges of flap 22, to add wear and strength characteristics thereto and to prevent any unnecessary irritation to the person/patient.

Generally, when fitting garment 2 to the person/patient, side straps 16, 16 attached at 18, 18 are pulled laterally by an attendant under the arms of the person/patient and then snugged about the person/patient prior to engaging a portion of receiving means 30. The side straps 16, 16 are preferably adjusted by the attendant to fit as close to the arms as possible to minimize the size of the arm openings for the person/patient. Interior surfaces 16a, 16a and exterior surfaces 16b, 16b of side straps 16, 16 are preferably smooth and non-irritating to the person/patient.

Subsequent to the side straps 16, 16 being secured to receiving means 30, flap 22 is made to cover the fastened side straps 16, 16 prior to fastening means 28 being engaged with another portion of receiving means 30 by the attendant. Generally, the side straps 16, 16 are of sufficient length to substantially engage receiving means 30 without traversing the entire width of panel 4 or beyond, so that covering flap 22 fully covers the attached portion of straps 16, 16 depending upon the body size of the person/patient. Preferably side straps 16, 16 are snugged and extended in an upwardly direction when fastened to receiving means 30, and preferably flap 22 is snugged over the fastened side straps 16, 16 prior to engaging fastening means 28 to receiving means 30.

The garment 2 is now secured about the person/patient at its upper region, thereby leaving the lower region thereof to be fitted and secured about the person/patient while establishing the degree of restraint for the person/patient.

Tying straps 12, 12 extending laterally from the channel or pocket 4b at the lower region of panel 4, are introduced to the receiving means comprising at least two pair of strap-holding loops 32, 32 and 34, 34 located on the lower region 4c of panel 4 to fit and to secure the lower regions 4b and 4c of panel 4 about the person/patient. The pattern of introduction of tying straps 12, 12 to strap-holding loops 32, 32 and 34, 34, may vary, depending upon the degree of restraint required for the person/patient.

FIG. 3 shows each of tying straps 12, 12 passing through two loops, i.e. through one of the pair of loops 34, 34 and thereafter through one of the pair of loops 32, 32, prior to being secured to a structure out of reach of the person/patient, to allow some degree of rotation, whether in the supine or sitting position. Tying straps 12, 12 may also be employed to engage all of the loops 32, 32 and 34, 34 (not shown) to restrict rotational movement of the person/patient, whether in the supine or sitting position, prior to being secured to a structure out of reach of the person/patient, such as a bed frame or chair frame. Alternatively, tying straps 12, 12 may be employed to engage one or three of the loops 32, 32 or 34, 34 (not shown) or be employed in other variations depending upon the degree of restraint desired.

Figure 4:
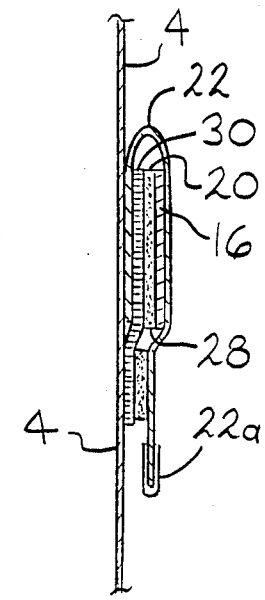
FIG. 4 is a sectional view along line 4—4 in FIG. 3.

Referring to FIG. 4, a cross-section of the flexible locking means is shown to more clearly describe the cooperation and relationship of the elements working in combination, wherein it has been found that longitudinal forces acting upon the straps, whether compressive or tensile forces, will not effect detachment of the flexible locking means within the limitations of even very strong persons/patients.

Flap 22, having binding 22a thereon, is attached to panel 4, and receiving means 30 is shown covering a portion of the material comprising flap 22. Fastening means 20 of strap 16 is shown in engaging relationship with one portion of receiving means 30, and fastening means 28 of flap 22 is shown in engaging relationship with another portion of receiving means 30, whereby flap 22 in the engaged position, i.e. during the operative mode, provides a protective covering channel to accommodate strap 16 in a locking relationship to panel 4 via the interacting relationships of the above elements.

When the flexible locking means is in the operative mode, out of reach of the person/patient, the latter is unable to defeat the former, yet the flexible locking means is substantially flat so as not to interfere with the comfort of the person/patient. However, when an attendant desires to release the flexible locking means, a "ripping" or "tearing" action is required by exerting a transverse force in relation to the attached straps, generally upward, upon flap 22 by tugging on binding 22a. Such action by the attendant will disengage fastening means 28 from receiving means 30 to restore flap 22 to the open position, thus exposing strap 16. A subsequent similar action by the attendant upon strap 16 will disengage fastening means 20 from receiving means 30 to allow panel 4 to freely drape upon the person/patient or to be removed from the person/patient.

Modifications of the disclosed article may be resorted to without departing from the spirit and scope of the appended claims.

I claim:

1. In a patient restraint garment comprising a flexible panel with an opening to receive the head and neck of a patient to allow said panel to drape about the upper torso of the patient and form an anterior portion and a posterior portion, said panel further comprising tying straps, fasteners, and receiving means to engage said tying straps, which tying straps are for subsequent securement to a structure out of reach of the patient, the improvement comprising in combination with said panel:
    (a) a pair of flexible fastening straps, attached to and extending laterally from opposite sides of said anterior portion of said panel at the approximate chest level of the patient for extension under the arms and about the patient, each of said straps having a surface including fastening means attached thereto for engagement with said posterior portion in the approximate upper back region of the patient out of reach of the patient;
    (b) a flexible flap attached to the said posterior portion of the said panel along a transverse line in said approximate upper back region of the patient, said flap having an interior surface further comprising fastening means attached thereto for engagement with said posterior portion of said panel; and
    (c) a receiving means attached to said posterior portion of said panel in said approximate upper back region of the patient for engagement of said fastening means of said fastening straps, and for engagement of said flexible flap overlapping said engaged fastening straps;
    to provide a flexible locking means comprising cooperating relationships between said straps, flap, receiving means, and panel, whereby said anterior portion and said posterior portion of said panel can be custom fitted against the upper torso of the patient while adjustably forming an arm hole of desired size on each side of said garment to limit the ability of the patient to defeat said garment.

2. The patient restraint garment as claimed in claim 1, wherein said anterior portion of said garment includes a lower area and wherein said tying straps are attached to said lower area of said anterior portion of said panel and extend laterally from opposite sides of said anterior portion of said panel for extension about the patient and engagement with said lower area of said posterior portion.

3. The patient restraint garment as claimed in claim 1, wherein said receiving means to engage said tying straps comprises two pairs of strap holding loops attached to said lower area of said posterior portion of said panel in a spaced relation to each other, thereby enabling reception of said tying straps in a plurality of configurations.

4. The patient restraint garment as claimed in claim 3, wherein one of said pair of loops is slightly spaced and is disposed proximal to and on opposite sides of the central longitudinal axis of said panel and the other of said pair of loops is substantially spaced and is disposed distal to and on opposite sides of said central longitudinal axis of said panel.

5. The patient restraint garment as claimed in claim 3, wherein one of said tying straps engages one of said distal loops and one of said proximal loops and the other of said tying straps engages the other of said distal loops and the other of said proximal loops in opposed direction, to enable said lower areas of said anterior portion and said posterior portion to be snugged about the patient, thereby enabling the patient to roll approximately 90° in either direction, after said tying straps are secured to said structure.

6. The patient restraint garment as claimed in claim 3, wherein one of said tying straps engages all of said distal loops and all of said proximal loops in one direction, and the other of said tying straps engages all of said distal loops and all of said proximal loops in the other direction, to enable said lower areas of said anterior portion and said posterior portion to be snugged about the patient, thereby restricting the motion of the patient from rolling in either direction, after said tying straps are secured to said structure.

7. The patient restraint garment as claimed in claim 1, wherein said flexible straps generally extend under the arms and about the patient in an upwardly direction for engagement with said receiving means attached to said posterior portion of said panel in said approximate upper back region of the patient, to thereby make it substantially impossible for the patient to disrupt said flexible locking means by unfastening said flap and/or said fastening straps.

8. The patient restraint garment as claimed in claim 7, wherein said flexible straps are in opposed positions on said receiving means.

9. The patient restraint garment as claimed in claim 7, wherein said flexible straps are positioned in a generally side-by-side position on said receiving means.

10. The patient restraint garment as claimed in claim 1, wherein said fastening means on said flap is attached distal to said attachment of said flap to said posterior portion of said panel, to allow various degrees of snugging of said flap in overlapping relation with said engaged fastening straps.

11. The patient restraint garment as claimed in claim 1, wherein said flap comprises at least one pair of spaced apart fastening means, to enable said fastening means to straddle said engaged fastening straps on said receiving means.

12. The patient restraint garment as claimed in claim 1, wherein said transverse line is established at a level proximal to the axillae regions of the patient, out of reach of the patient.

* * * * *